US011339651B2

United States Patent
Anifowose et al.

(10) Patent No.: US 11,339,651 B2
(45) Date of Patent: May 24, 2022

(54) SYSTEMS AND METHODS FOR GENERATING CONTINUOUS GRAIN SIZE LOGS FROM PETROGRAPHIC THIN SECTION IMAGES

(71) Applicant: Saudi Arabian Oil Company, Dhahran (SA)

(72) Inventors: Fatai A. Anifowose, Al-Khobar (SA); Mokhles M. Mezghani, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 111 days.

(21) Appl. No.: 16/789,988

(22) Filed: Feb. 13, 2020

(65) Prior Publication Data
US 2021/0254457 A1 Aug. 19, 2021

(51) Int. Cl.
E21B 49/00 (2006.01)
G06T 7/50 (2017.01)
G06T 7/174 (2017.01)
E21B 47/002 (2012.01)
(Continued)

(52) U.S. Cl.
CPC ............ *E21B 49/00* (2013.01); *E21B 47/002* (2020.05); *E21B 49/02* (2013.01); *G01N 33/24* (2013.01);
(Continued)

(58) Field of Classification Search
CPC ........ E21B 49/00; E21B 49/02; E21B 47/002; G01V 11/00; G01N 33/24; G06T 7/40; G06T 7/50; G06T 7/174; G06T 5/50
See application file for complete search history.

(56) References Cited

U.S. PATENT DOCUMENTS 4,868,883 A 9/1989 Chen
7,066,019 B1 6/2006 Papanastasiou
(Continued)

FOREIGN PATENT DOCUMENTS

| AU | 2017279838 B1 | 9/2018 |
| CN | 105781536 A | 7/2016 |
| WO | 2019023126 A1 | 1/2019 |

OTHER PUBLICATIONS

Francus, "An image-analysis technique to measure grain-size variation in thin sections of soft elastic sediments," Sedimentary Geology, 121, pp. 289-298 (Year: 1998).*
(Continued)

*Primary Examiner* — John Fitzgerald
(74) *Attorney, Agent, or Firm* — Bracewell LLP; Constance G. Rhebergen; Brian H. Tompkins (57) ABSTRACT

Systems and methods for determining a continuous grain size log from a collection of petrographic thin section images are provided. Thin section images from core samples from one or more wells may be obtained and analyzed to estimate grain sizes. Using wireline logs from the one or more wells and the estimated grain sizes, a data structure (for example, a database) of grain sizes and wireline logs at depths may be constructed. The data structure may be used to train a machine learning model. Next, a wireline tool may be used to obtain wireline logs in a new well, and a continuous grain size log may be determined from the wireline logs of using the machine learning model. Computer-readable media for determining reservoir rock grain sizes from a collection of petrographic thin section images is also provided.

18 Claims, 6 Drawing Sheets

(51) Int. Cl.
*E21B 49/02* (2006.01)
*G01N 33/24* (2006.01)
*G01V 11/00* (2006.01)
*G06T 5/50* (2006.01)
*G06T 7/40* (2017.01)

(52) U.S. Cl.
CPC ............... *G01V 11/00* (2013.01); *G06T 5/50* (2013.01); *G06T 7/174* (2017.01); *G06T 7/40* (2013.01); *G06T 7/50* (2017.01); *G06T 2207/10028* (2013.01); *G06T 2207/20221* (2013.01)

(56) References Cited

U.S. PATENT DOCUMENTS

| | | | |
|---|---|---|---|
| 9,507,047 | B1 | 11/2016 | Dvorkin et al. |
| 9,626,771 | B2 * | 4/2017 | Mezghani ............... G06T 7/73 |
| 9,684,084 | B2 | 6/2017 | Sung et al. |
| 9,939,548 | B2 * | 4/2018 | Burmester ............ G01V 11/00 |
| 10,620,340 | B2 * | 4/2020 | Andersen ............... G06F 30/20 |
| 11,010,883 | B2 * | 5/2021 | Anifowose .......... G06K 9/6218 |
| 2007/0133866 | A1 * | 6/2007 | Chang ..................... G06K 9/00 382/159 |
| 2007/0239359 | A1 | 10/2007 | Stelting et al. |
| 2013/0080133 | A1 | 3/2013 | Sung et al. |
| 2014/0149041 | A1 | 5/2014 | Sung et al. |
| 2015/0234863 | A1 * | 8/2015 | Lilje .................. G06K 9/00637 382/103 |
| 2015/0241591 | A1 * | 8/2015 | Burmester ............... G06K 9/64 702/7 |
| 2016/0328419 | A1 | 11/2016 | Safonov et al. |
| 2016/0343150 | A1 * | 11/2016 | Mezghani ............. G06K 9/6232 |
| 2017/0091958 | A1 * | 3/2017 | Mezghani ............ G02B 21/365 |
| 2017/0286802 | A1 * | 10/2017 | Mezghani .............. G06K 9/627 |
| 2018/0100390 | A1 * | 4/2018 | Patil ....................... E21B 25/00 |
| 2018/0112478 | A1 | 4/2018 | Goloshchapova |
| 2018/0347354 | A1 | 12/2018 | Li et al. |
| 2019/0025461 | A1 | 1/2019 | Wiener et al. |
| 2019/0318467 | A1 * | 10/2019 | Anifowose .......... G02B 21/365 |
| 2021/0041596 | A1 * | 2/2021 | Kushwaha ............ G06F 30/27 |
| 2021/0157116 | A1 * | 5/2021 | Mezghani ................ G06T 9/40 |

OTHER PUBLICATIONS

Basu et al., "Facies analysis: Integration of core and log data using a neural network as input for reservoir modeling in Betty Field, Malaysia," XP-001210333 (Year: 2004).*

Qi et al., "Neural Network prediction of carbonate lithofacies from well logs, Big Bow and Sand Arroyo Creek Fields, Southwest Kansas," Computers & Geosciences 32, pp. 947-964 (Year: 2006).*

Goodchild, "Geological Image Processing of Petrographic Thin Sections Using the Rotating Polarizer Stage," Thesis, Brock University, St. Catherines, Ontario (Year: 1998).*

Goodchild et al., "Edge Detection in Petrographic Images Using The Rotating Polarizer Stage," Computers & Geosciences, 24, pp. 745-751 (Year: 1998).*

Fuenten, "A Computer-Controlled Rotating Polarizer Stage for the Petrographic Microscope," Computers & Geosciences, 23, 2, pp. 203-208 (Year: 1997).*

Asmussen, Pascal et al.; "Semi-automatic segmentation of petrographic thin section images using a "seeded-region growing algorithm" with an application to characterize wheathered subarkose sandstone" Comp. & Geosci. 83 (2015); pp. 89-99.

Borazjani, Omid et al.; "Two intelligent pattern recognition models for automatic identification of textural and pore space characteristics of the carbonate reservoir rocks using thin section images" J. of Natural Gas Sci. & Eng. 35 (2016); pp. 944-955.

Budennyy, Semen et al.; "Image Processing and Machine Learning Approaches for Petrographic Thin Section Analysis" SPE-187885-MS, Russian Petroleum Technology Conference, Oct. 16-18, 2017; pp. 1-12.

Buscombe, D. et al.; "A universal approximation of grain size from images of noncohesive sediment" Journal of Geophysical Research, vol. 115, F02015 (2010); pp. 1-17.

Ghiasi-Freez, Javad et al.; "Semi-automated porosity identification from thin section images using image analysis and intelligent discriminant classifiers" Computers & Geosciences 45 (2012); pp. 36-45.

Graciolli, Vinicius Medeiros; "A Novel Classification Method Applied to Well Log Data Calibrated by Ontology-based Core Descriptions" Universidade Federal Do Rio Grande Do Sul Inst. De Informática Programa De Pós-Graduação Em Computção, Feb. 2018; 64 pg.

Jungmann, Matthias et al.; "Segmentation of thin section images for grain size analysis using region competition and edge-weighted region merging" Computers & Geosciences 72 (2014); pp. 33-48.

Kellerhals, Rolf et al.; "On Grain Size from Thin Sections" The Journal of Geology, vol. 83, No. 1 (Jan. 1975); pp. 79-96.

International Search Report and Written Opinion for International Application No. PCT/US2021/017983 report dated May 27, 2021; pp. 1-13.

* cited by examiner

SYSTEMS AND METHODS FOR GENERATING CONTINUOUS GRAIN SIZE LOGS FROM PETROGRAPHIC THIN SECTION IMAGES

BACKGROUND

Field of the Disclosure

The present disclosure generally relates to the production of hydrocarbons from hydrocarbon reservoirs in rock formations. More specifically, embodiments of the disclosure relate to estimating the grain size of reservoir rock in such formations.

Description of the Related Art

An understanding of the subsurface material within a hydrocarbon reservoir may play an important role in development of the hydrocarbon reservoir to produce hydrocarbons such as oil and gas. More specifically, an ability to identify rock types and their associated properties—such as grain size—of subsurface material may significantly enhance development of the hydrocarbon reservoir. Existing techniques estimate grain size from samples extracted from specific locations in wells drilled to access a reservoir. However, the results from these techniques are usually considered to be non-representative of a location in a reservoir and may not be usable in further analysis of the reservoir.

SUMMARY

Conventionally, grain size estimations are obtained from visual analysis of thin section samples of rock from a hydrocarbon reservoir in a formation. Core samples (also referred to as "core plugs" are typically obtained from certain locations in a well drilled in a formation to access a hydrocarbon reservoir. Thin section samples may then be prepared from these core samples. However, due to the pore scale resolution of thin section analyses, the results from the analyses may not accurately represent a location in the reservoir.

In one embodiment, a method for determining grain size of reservoir rock in a hydrocarbon reservoir is provided. The method includes extracting a plurality of core samples from a first well, each core sample extracted from a different depth in the well, cutting a respective plurality of sections from the plurality of core samples, and determining a grain size from each section of the plurality of sections to determine a plurality of discrete grain sizes at a respective plurality of depths in the first well. The method also includes obtaining a first wireline log from the first well, combining the first wireline log and the plurality of discrete grain sizes at the plurality of depths in the first well to produce a structured data set, and generating a machine learning model using the structured data set. The method further includes inserting a wireline tool into a second well, generating a second wireline log from measurements obtained using the wireline tool, and determining, using the second wireline log and the machine learning model, a continuous grain size log having a plurality of grain sizes and a respective plurality of continuous depths in the second well.

In some embodiments, obtaining a first wireline log from the first well includes inserting a wireline tool into the first well and generating the first wireline log from measurements obtained using the wireline tool. In some embodiments, the first wireline log includes at least one of a gamma ray (GR) log, a neutron porosity (NPHI) log, a sonic (DT) log, a deep resistivity (RTD) log, a shallow resistivity (RTS) log, and a density (RHOB) log. In some embodiments, the second wireline log includes at least one of a gamma ray (GR) log, a neutron porosity (NPHI) log, a sonic (DT) log, a deep resistivity (RTD) log, a shallow resistivity (RTS) log, and a density (RHOB) log. In some embodiments, the machine learning model is an artificial neural network (ANN), a support vector machine (SVM), a radial basis function (RBF), fuzzy logic, or a decision tree. In some embodiments, each section of the plurality of sections has a thickness of 30 microns. In some embodiments, determining a grain size from each section of the plurality of sections to determine a plurality of grain sizes at a plurality of depths in the first well includes combining images of the section acquired with plane-polarized light and cross-polarized light to produce a textural analysis image, segmenting grains from the textural analysis image based on different regions determined from a compositional analysis image of the section, and determining a grain size of one of the segmented grains. In some embodiments, determining a grain size from each section of the plurality of sections to determine a plurality of grain sizes at a plurality of depths in the first well includes using point counting.

In another embodiment, a system for determining a grain size of reservoir rock in a hydrocarbon is provided. The system includes a plurality of sections cut from a respective plurality of core samples from a first well, each core sample extracted from a different depth in the first well, the plurality of sections used to estimate a grain size from each section of the plurality of sections to produce a plurality of discrete grain sizes at a respective plurality of depths in the first well. The system further includes a first wireline log from the first well and a non-transitory computer-readable medium, the medium having executable code stored thereon. The executable code includes a set of instructions that causes a processor to perform operations that include combining the first wireline log and the plurality of discrete grain size at the respective plurality of depths in the first well to produce a structured data set, generating a machine learning model using the structured data set, receiving a second wireline log from a second well, and determining, using the second wireline log and the machine learning model, a continuous grain size log that includes a plurality of grain sizes and a respective plurality of continuous depths in the second well.

In some embodiments, the first wireline log includes at least one of a gamma ray (GR) log, a neutron porosity (NPHI) log, a sonic (DT) log, a deep resistivity (RTD) log, a shallow resistivity (RTS) log, and a density (RHOB) log. In some embodiments, the second wireline log includes at least one of a gamma ray (GR) log, a neutron porosity (NPHI) log, a sonic (DT) log, a deep resistivity (RTD) log, a shallow resistivity (RTS) log, and a density (RHOB) log. In some embodiments, the machine learning model is an artificial neural network (ANN), a support vector machine (SVM), a radial basis function (RBF), fuzzy logic, or a decision tree. In some embodiments, the system includes a wireline tool operable to generate the second wireline log. In some embodiments, the structured data set is a database. In some embodiments, each section of the plurality of sections has a thickness of 30 microns.

In another embodiment, a non-transitory computer-readable medium, the medium having executable code stored thereon is provided. The executable code includes a set of instructions that causes a processor to perform operations that include receiving a plurality of estimated grain sizes, each grain size estimated from a section of the plurality of sections cut from a respective plurality of core samples from a first well, each core sample extracted from a different depth in the first well, and receiving a first wireline log from the first well. The operations also include combining the first wireline log and the plurality of discrete grain sizes at a respective plurality of depths in the first well to produce a structured data set and generating a machine learning model using the structured data set. Finally, the operations include receiving a second wireline log from a second well and determining, using the second wireline log and the machine learning model, a continuous grain size log includes a plurality of grain sizes and a respective plurality of continuous depths in the second well.

In some embodiments, the first wireline log includes at least one of a gamma ray (GR) log, a neutron porosity (NPHI) log, a sonic (DT) log, a deep resistivity (RTD) log, a shallow resistivity (RTS) log, and a density (RHOB) log. In some embodiments, the second wireline log includes at least one of a gamma ray (GR) log, a neutron porosity (NPHI) log, a sonic (DT) log, a deep resistivity (RTD) log, a shallow resistivity (RTS) log, and a density (RHOB) log. In some embodiments, the machine learning model is an artificial neural network (ANN), a support vector machine (SVM), a radial basis function (RBF), fuzzy logic, or a decision tree. In some embodiments, the structured data set is a database.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments includes systems, methods, and computer-readable media for determining continuous grain size logs for a well from a collection of petrographic thin section images. Thin section images may be obtained from core samples from one or more wells. The thin section images may be analyzed to estimate reservoir rock discrete grain sizes at depths in the one or more wells. Wireline logs from the one or more wells may also be obtained. Using the wireline logs and the estimated grain sizes, a structured data set (for example, a database) of discrete grain sizes and wireline logs at depths may be constructed. The structured data set may be used to generate a grain size machine learning model. A wireline tool may be used to obtain wireline logs in a new well (for example, well for which core samples are unavailable). A continuous grain size log having grain sizes at continuous depths in the new well may be determined from the wireline logs of the new well using the machine learning model.

Figure 1:
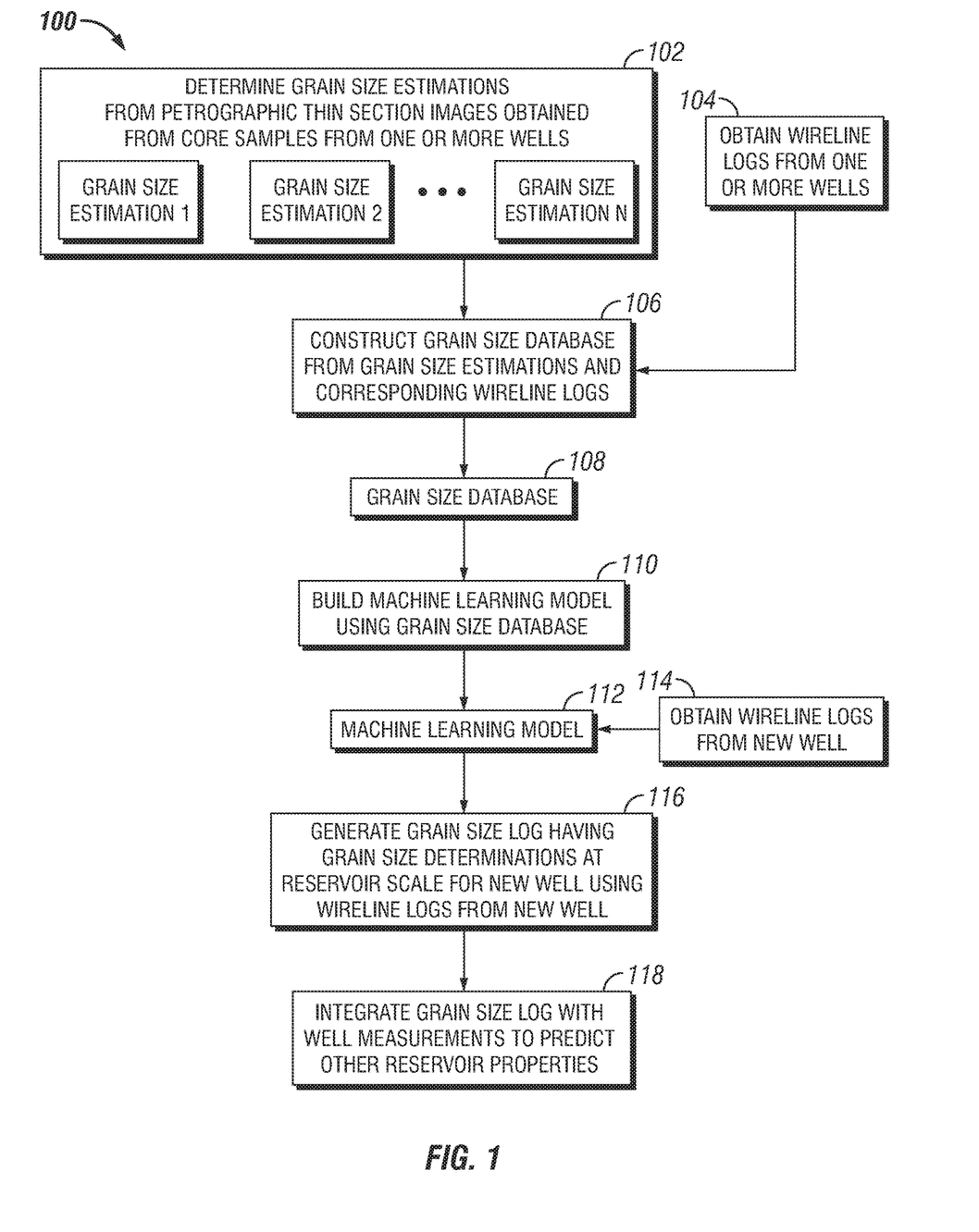
FIG. 1 is a block diagram of a process for determining reservoir rock grain size from a collection of petrographic thin section images in accordance with an embodiment of the disclosure.
Figure 2:
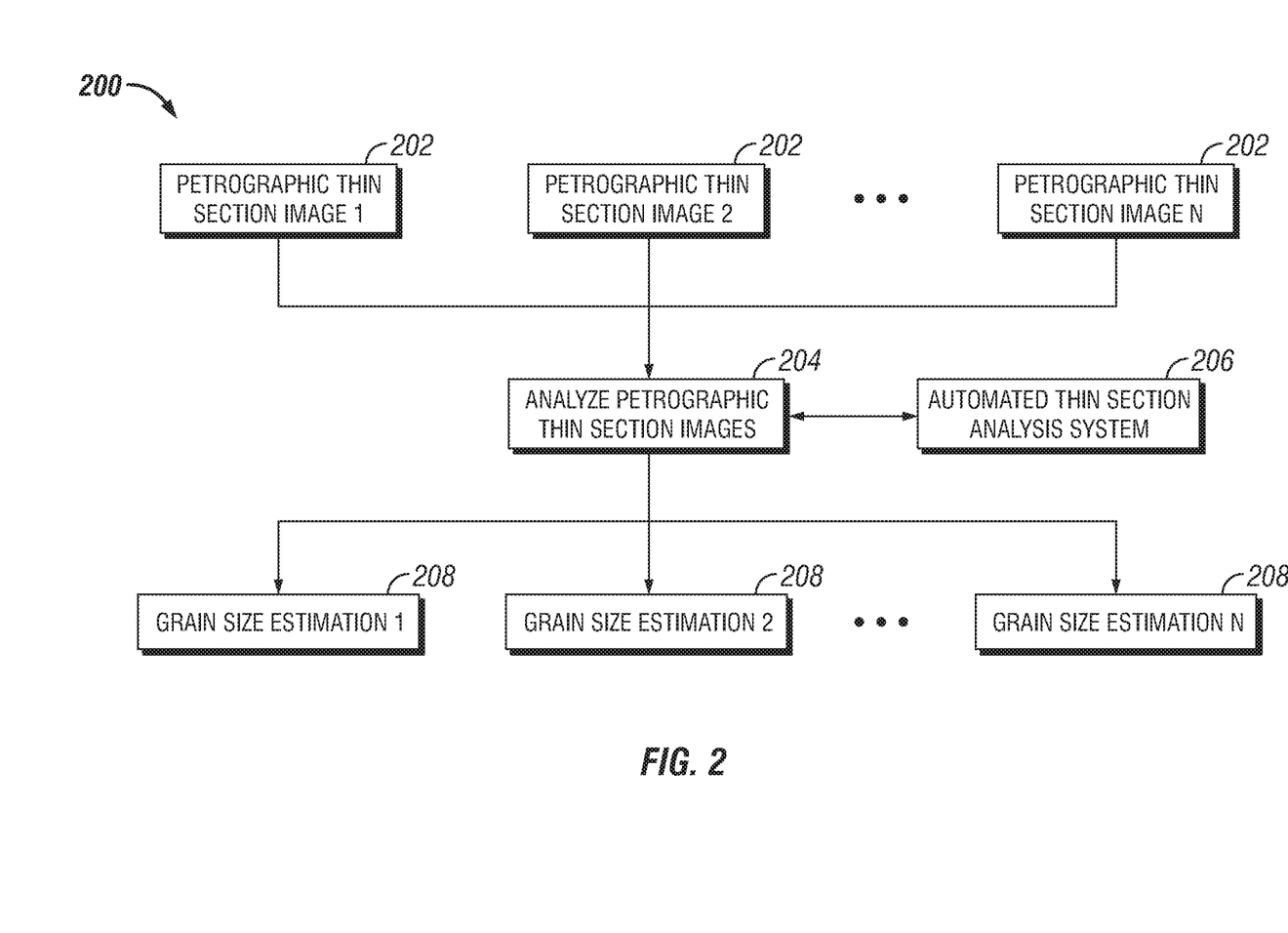
FIG. 2 is a block diagram of a process for estimating discrete grain sizes at depths from petrographic thin section images in accordance with an embodiment of the disclosure.

FIG. 1 depicts a process 100 for determining continuous grain size logs for a well from a collection of petrographic thin section images in accordance with an embodiment of the disclosure. Initially grain size estimations from petrographic thin section images are obtained (block 102). For example, as shown in FIG. 1, n number of grain size estimations may be obtained. The petrographic thin section images are images of thin sections obtained from core samples from one or more wells. As described in the disclosure, the grain size estimation may be a conventional visual analysis or, as shown in FIG. 2 and described supra, an automated analysis performed on the petrographic thin section images.

Additionally, wireline logs from the one or more wells may be obtained (block 104). For each depth of the grain size estimations, corresponding wireline logs may be obtained. The wireline logs may include gamma ray (GR), neutron porosity (NPHI), sonic (DT), deep resistivity (RTD), shallow resistivity (RTS), and density (RHOB) logs.

Figure 3:
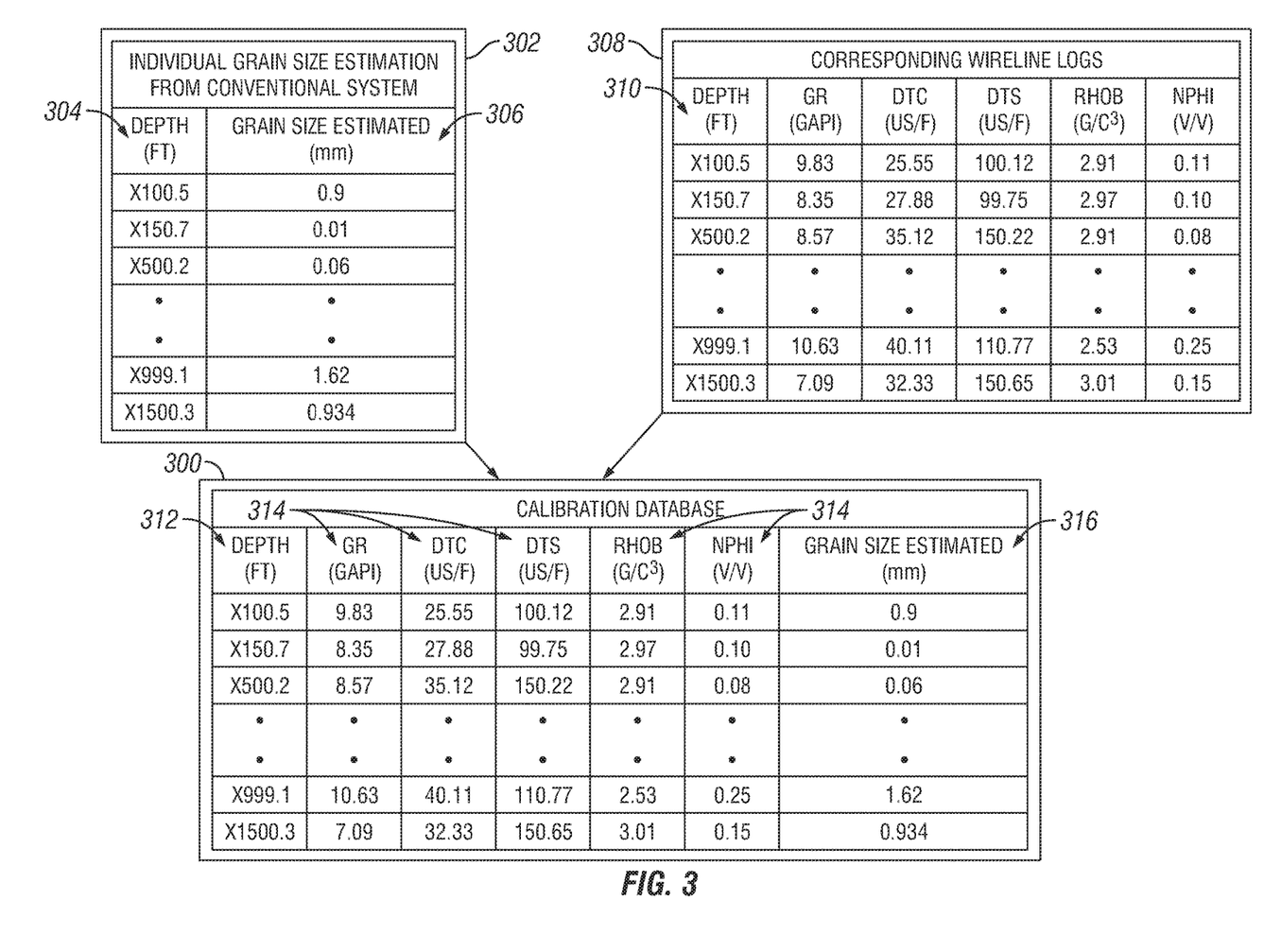
FIG. 3 is a block diagram of an example wireline log and grain size structured data set in accordance with an embodiment of the present disclosure.

A grain size and wireline log data structure 108 may be constructed from the grain size estimations and the corresponding wireline logs (block 106). An example grain size and wireline log data structure is illustrated in FIG. 3 and described supra. The grain size and wireline log data structure 108 is used to construct a grain size machine learning model (block 110). The construction and operation of the grain size machine learning model 112 is described supra with reference to FIGS. 4A and 4B.

Next, wireline logs for a new well may be obtained (block 114). For example, the new well may be drilled to access a previously drilled hydrocarbon reservoir or a new hydrocarbon reservoir of interest. The wireline logs may include gamma ray (GR), neutron porosity (NPHI), sonic (DT), deep resistivity (RTD), shallow resistivity (RTS), and density (RHOB) logs. Using the wireline logs for the new well, a continuous grain size log having grain sizes at the reservoir scale for the new well may be determined by the machine learning model (block 116). In some embodiments, the grain size log may be integrated with measurements from the new well to predict other properties of a hydrocarbon reservoir (block 118).

FIG. 2 depicts a process 200 for estimating discrete grain sizes at specific depths from petrographic thin section images in accordance with an embodiment of the disclosure. The grain size estimations may be used as inputs to the process 100 illustrated in FIG. 1. Initially, petrographic thin section images 202 from one or more wells may be obtained. For example, as shown in FIG. 2, n number of petrographic thin section images may be obtained. The petrographic thin section images are obtained from thin section samples. The thin section samples may be prepared from core plugs extracted from the one or more wells during drilling.

As will be appreciated, the core plugs may be obtained using a coring tool that obtains a reservoir rock sample from a formation accessed via a well. A coring tool may be inserted in and retrieved from a wellbore of a well using a conveyance system that facilitates transporting the coring tool and enables communication (for example, electrical and data communications) between the coring tool and surface systems. The conveyance system may include a wireline system, a drill pipe system, a coiled tubing (CT) system, tractor conveyance device, or other suitable systems.

The coring tool may be connected to a control system that provides for monitoring and controlling sampling operations using the coring tool. For example, the coring tool control system may control the conveyance system based on feedback provided by the conveyance system and the coring tool. The feedback may include, for example, depth measurements returned from conveyance system, data received from the coring tool, or both.

The coring tool may include various components to enable collection and preservation of core samples. In some embodiments, the core samples may be a continuous core sample or a sidewall core sample. For example, the coring tool may include a core barrel and a core bit. In another example, the coring tool may include a percussion or rotary sidewall coring device.

In some embodiment, the petrographic thin section images may be produced by obtaining thin section samples and producing digital images of the thin section samples using a high-resolution polarizing microscope. The petrographic thin section samples may be produced by cutting raw samples from the core plug using a diamond saw and physically processing (grinding, polishing, or both) the raw sample to produce the thin section sample. As will be appreciated, the term "thin section" refers to sections having a thickness of about 30 microns or less. In some embodiments, the thin section samples may be impregnated with a staining material (for example, a colored epoxy) and additionally processed (for example, polished and mounted on a slide) before obtaining images using the high-resolution polarizing microscope.

Next, the obtained petrographic thin section images may be analyzed to estimate grain size (204). In some embodiments, the grain size may be estimated using an automated thin section analysis system, using a conventional point counting technique as known in the art, or other techniques.

As shown in FIG. 2, in some embodiments, the analysis may be performed by an automated thin section analysis system 206, such as that described in U.S. application Ser. No. 15/955,072 titled "AUTOMATED ANALYSIS OF PETROGRAPHIC THIN SECTION IMAGES USING ADVANCED MACHINE LEARNING TECHNIQUES," now U.S. Pat. No. 11,010,883, a copy of which is incorporated by reference in its entirety for purposes of United States Patent Practice. The automated thin section analysis system 206 may process a plane-polarized thin section image of a thin section sample and one, two, three, or four cross-polarized images of the thin section sample each taken at different angles. By comparing the plane plane-polarized thin section image of a thin section sample with one or more of the cross-polarized images, a grain size of the thin section may be estimated. A more detailed discussion of an example automated thin section analysis system 206 is provided infra.

Initially, the automated thin section analysis system 206 may use a compositional analysis image to determine compositional data of a thin section. The compositional analysis image may be an image of a thin section acquired with plane-polarized light, such as using a polarizing microscope. Such images may be referred to as plane-polarized (PPL) images of thin sections. A feature vector for each respective pixel of the compositional analysis image may be determined. The feature vector for each respective pixel of the compositional analysis image may include the color components corresponding to the respective pixel. For example, if the compositional analysis image is a luminosity-chromaticity image, then the feature vector for a respective pixel includes the values of the luminosity and chromaticity channels of the respective pixel. In some embodiments, the feature vector for each respective pixel of the compositional analysis image includes other features derived from the neighborhood of the respective pixel in the compositional analysis image, such as mean color intensities and variances of color intensities in neighborhoods of the respective pixel. The automated thin section analysis system 206 may determine the regions of the compositional analysis image corresponding to the respective thin section components (such as grains, pores, clays, and in some cases, iron oxides) by clustering the pixels of the compositional analysis image based on their feature vectors.

The automated thin section analysis system 206 may determine the compositional properties of the thin section based on the determined regions (that is, the regions corresponding to each different thin section component). The compositional properties of the thin section include the relative proportions of the thin section that are occupied by the different thin section components. Specifically, to determine the proportion of the thin section that is occupied by a component c, the system may compute the number of pixels in region c divided by the total number of pixels times 100%, where the component c may correspond to grains, pores, clays, iron oxides, heavy minerals, and any other relevant component.

The automated thin section analysis system 206 may determine a thin section textural analysis image using the compositional analysis image according to the process described infra. The automated section analysis system 206 may receive multiple images of a thin section generated by a polarizing microscope and clustered image components (indicating the regions of the thin section corresponding to the different thin section components).

The polarizing microscope is configured to generate the thin section images by acquiring magnified images of the thin section while exposing the thin section to linearly-polarized light (that is, light where the magnetic or electric field vector are confined to a plane along the direction of propagation). The thin section images include images of the thin section acquired when the polarizing microscope exposes the thin section to linearly-polarized light and images of the thin section acquired when the polarizing microscope exposes the thin section to cross-polarized light. Different thin section images may be acquired by rotating the position of the thin section in the polarizing microscope to different angles in the polarizing microscope relative to a reference angle and acquiring images of the thin section while it is rotated to the different angles. The different angles may include the angles 0°, 27.5°, 45°, 67.5°, or any other appropriate angles. The thin section images may be color images, that is, images that include color data from different color channels for each image pixel. For example, the thin section images may be RGB images, that is, images that include color data for a red color channel, a green color channel, and a blue color channel for each image pixel. As another example, the thin section images may be images that include color data for a luminosity channel and a chromaticity channel.

The automated thin section analysis system 206 may register the multiple thin section images to a reference thin section image, such as the compositional analysis image, using any appropriate registration algorithm. The registration algorithm may employ a linear registration transformation, an elastic registration transformation, or any other appropriate registration transformation. The registration algorithm may include a sum of squared differences objective function, a mutual information objective function, or any other appropriate objective function.

Each of the multiple thin section images may have been acquired while rotated to a different angle in the polarizing microscope. In some implementations, the automated thin section analysis system 206 may de-rotate each of the multiple thin section images relative to the reference thin section image prior to registering them to the reference thin section image. The automated thin section analysis system 206 may de-rotate a thin section image relative to the reference thin section image by determining the difference between the acquisition angle of the thin section image and the reference thin section image, and digitally rotating the thin section by the opposite of the determined angle. For example, if the automated thin section analysis system 206 determines that the difference between the acquisition angle of the thin section image and the reference thin section image is 35° clockwise, then the automated thin section analysis system 206 rotates the thin section image 35° counterclockwise.

The automated thin section analysis system 206 may combine the registered thin section images to generate a composite image. In some embodiments, prior to combining the registered thin section images, the automated thin section analysis system 206 may convert them to corresponding grayscale images. In some implementations, the automated thin section analysis system 206 may combine the registered thin section images by averaging them (that is, by setting the value of each pixel of the combined image to be the average of the values of the corresponding pixels of the registered thin section images). In some implementations, the automated thin section analysis system 206 may combine the registered thin images by computing their median (that is, by setting the value of each pixel of the combined image to be the median of the values of the corresponding pixels of the registered thin section images).

The automated thin section analysis system 206 may generate a mask image from the clustered image components. Specifically, the automated thin section analysis system 206 may generate a mask image of the grain component of the thin section, the pore component of the thin section, or both. A mask image of one or more components of a thin section refers to an image where pixels belonging to the one or more components have a first predetermined value (for example, the value of one) and pixels that do not belong to the one or more components have a second predetermined value (for example, the value of zero).

The automated thin section analysis system 206 may combine the composite image and the mask image to generate a textural analysis image. The masking assists in highlighting grains and enables effective segmenting of the grains in the resulting image. The composite image and the mask image may be combined in any appropriate manner. For example, the composite image and the mask image may be combined by setting the value of each pixel of the textural analysis image to be the product of the values of the corresponding pixels of the composite image and the mask image, thereby highlighting the grain region in the textural analysis image.

After generation of the textural analysis image, the textural analysis image may be further processed by the automated thin section analysis system 206 to determine grain sizes as part of grain texture data. The automated thin section analysis system 206 may segment the individual grains from the textural analysis image. Segmenting the grains from the textural analysis image may include generating data indexing the grains of the thin section (that is, data that associates each grain of the thin section to a different numerical index value) and data that indicates, for each respective pixel of the textural analysis image, either that the pixel does not correspond to a grain (that is, the pixel is a background pixel) or that the pixel corresponds to a particular grain of the thin section (that is, a grain indexed by a particular index value).

The automated thin section analysis system 206 may segment the grains using any appropriate segmentation algorithm. In general, the segmentation algorithm is an algorithm that is mainly automated (that is, an algorithm that requires little to no human intervention). For example, the automated thin section analysis system 206 may segment the grains from the textural analysis image using an image processing method, such as a watershed segmentation algorithm. In this example, the automated thin section analysis system 206 processes the textural analysis image to generate an edge image, where the intensity of a pixel is correlated to the likelihood that the pixel belongs to an edge of the textural analysis image. The edge image delineates the grains of the thin section, and a watershed segmentation algorithm is applied to the edge image to segment the grains. Generally, a watershed segmentation algorithms determines a segmentation of an image into different regions by determining regions of the image that are enclosed by boundaries characterized by high pixel intensities (for example, by a flooding algorithm). By way of other examples, the automated thin section analysis system 206 may segment the grains from the textural analysis image using machine learning segmentation methods, such as random forest or neural network segmentation methods.

The automated thin section analysis system 206 may determine the various properties that makeup the grain texture data of the segmented grains, such as one or more of the areas, the perimeters, the long axis diameters, the short axis diameters, and the roundness of the grains. The automated thin section analysis system 206 may individually process each of the segmented grains and determines the corresponding properties of the grain. For example, the automated thin section analysis system 206 may determine the area of a segmented grain by multiplying the number of pixels in the segmented grain by the area occupied by a single pixel. The grain texture data can indicate the diameters of the grains in the thin section and thus the discrete grain sizes of the grains in the thin section. For example, the average of certain grain texture data, such as the diameters of the grains, may represent the grain size for the depth location represented by the analyzed thin section.

In other embodiments, the analysis to estimate grain size may be a conventional point counting technique as is known in the art, such as by using a using a microscope and a electromechanical device to move the thin section image under analysis.

Discrete grain size estimations (block 208) at depths may be produced by the analysis of obtained petrographic thin section images. A grain size estimation may be produced for each analyzed petrographic thin section image, such that n number of grain size estimations are produced for the n number of petrographic thin section images. Each grain size estimation may be associated with a discrete depth in the well from which the thin section sample (and corresponding core sample) used to estimate the grain size was extracted.

FIG. 3 depicts an example of a grain size and wireline log structure (for example, grain size and wireline log database 300) used by the machine learning model in accordance with an embodiment of the present disclosure. As described in the disclosure, individual grain size estimations 302 may be determined using the techniques described supra, such as illustrated in FIG. 2. As shown in FIG. 3, the grain size estimations data may include specific depths 304 (for example, in feet (ft)) in a well and an estimated grain size 306 (for example, in millimeters (mm)) at a respective depth in the well. For example, at a depth of 100.5 ft, the estimated grain size is 0.9; at depth of 150.7 ft, the estimated grain size is 0.01 mm; and so on as shown in FIG. 3.

As also discussed, corresponding wireline logs 308 at specific depths 310 in the well are also used to produce the grain size and wireline log database 300. In the example embodiment depicted in FIG. 3, the wireline logs 308 include gamma ray (GR, measured in Gammaray American Petroleum Institute (API) or "GAPI" units), compressional sonic travel time (DTC, measured in microseconds per foot (μs/ft), shear sonic travel time (DTS, measured in μs/ft, density (RHOB, measured in grams per cubic centimeter (g/c³), and neutron porosity (NPHI, expressed in near-to-far neutron count ratio (V/V)). In other embodiments, the wireline logs 308 may omit one or more of the measurements shown in FIG. 3, or may include additional or alternative measurements. The wireline logs 308 are provide at a respective depth in the well. For example, at a depth of 100.5 ft, the GR log is 9.83 GAPI, the DTC log is 25.55 μs/ft, the DTS log is 100.12 μs/ft, the RHOB log is 2.91 g/c³, and the NPHI log is 0.11 V/V.

The grain size and wireline log database 300 shown in FIG. 3 is constructed from the grain size estimations 302 and the corresponding wireline logs 308. The grain size and wireline log database 300 may include a specific depth 312 with corresponding wireline logs 314 and grain size estimations 316 at a respective depth. For example, at a depth of 150.7 ft, the GR log is 8.35 GAPI, the DTC log is 27.88 μs/ft, the DTS log is 99.75 μs/ft, the RHOB log is 2.97 g/c³, the NPHI log is 0.10 V/V, and the estimated grain size is 0.01 mm. The grain size and wireline log database 300 may be used to construct a grain size machine learning model as described infra.

Figure 4A:
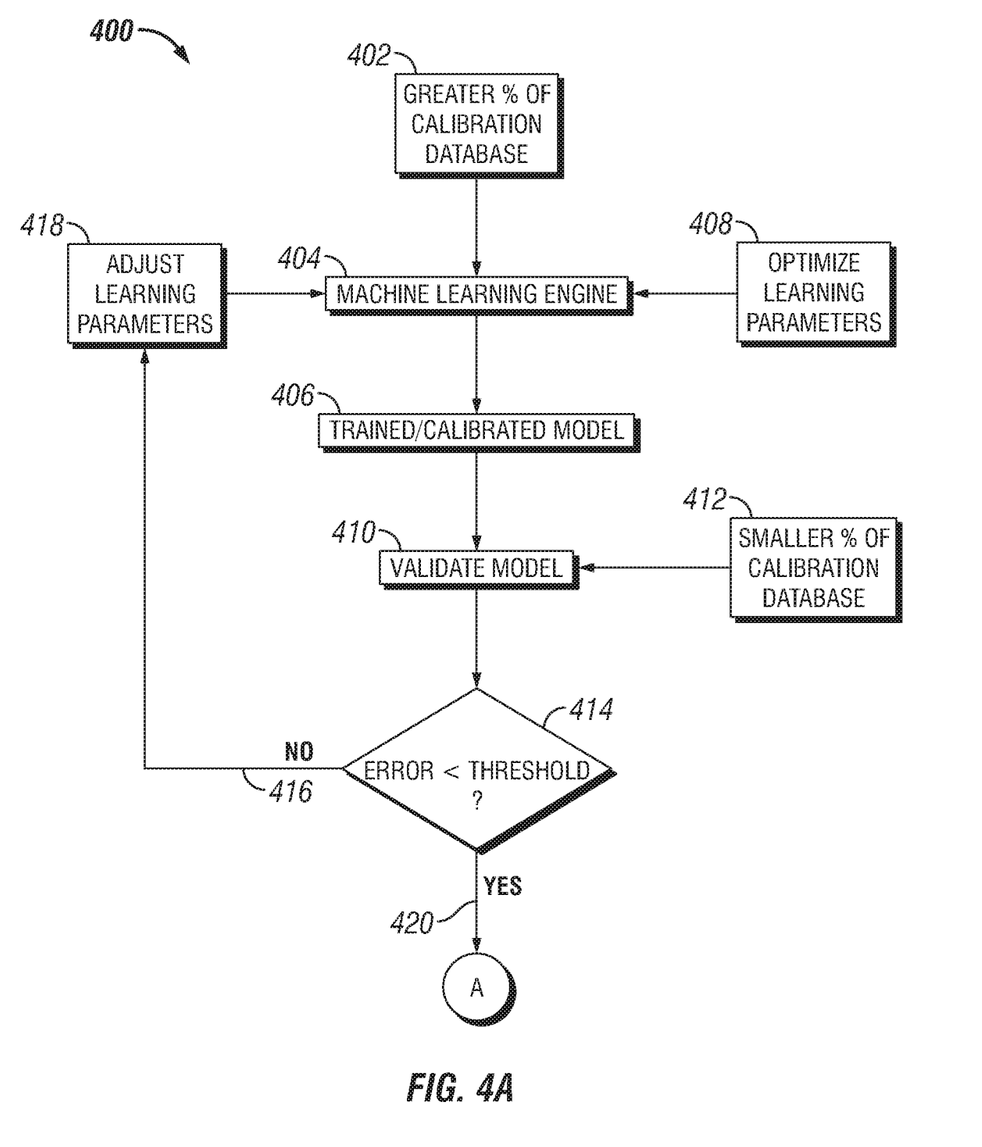
FIGS. 4A and 4B depict a process for illustrating operation of a machine learning model in accordance with an embodiment of the disclosure.
Figure 4B:
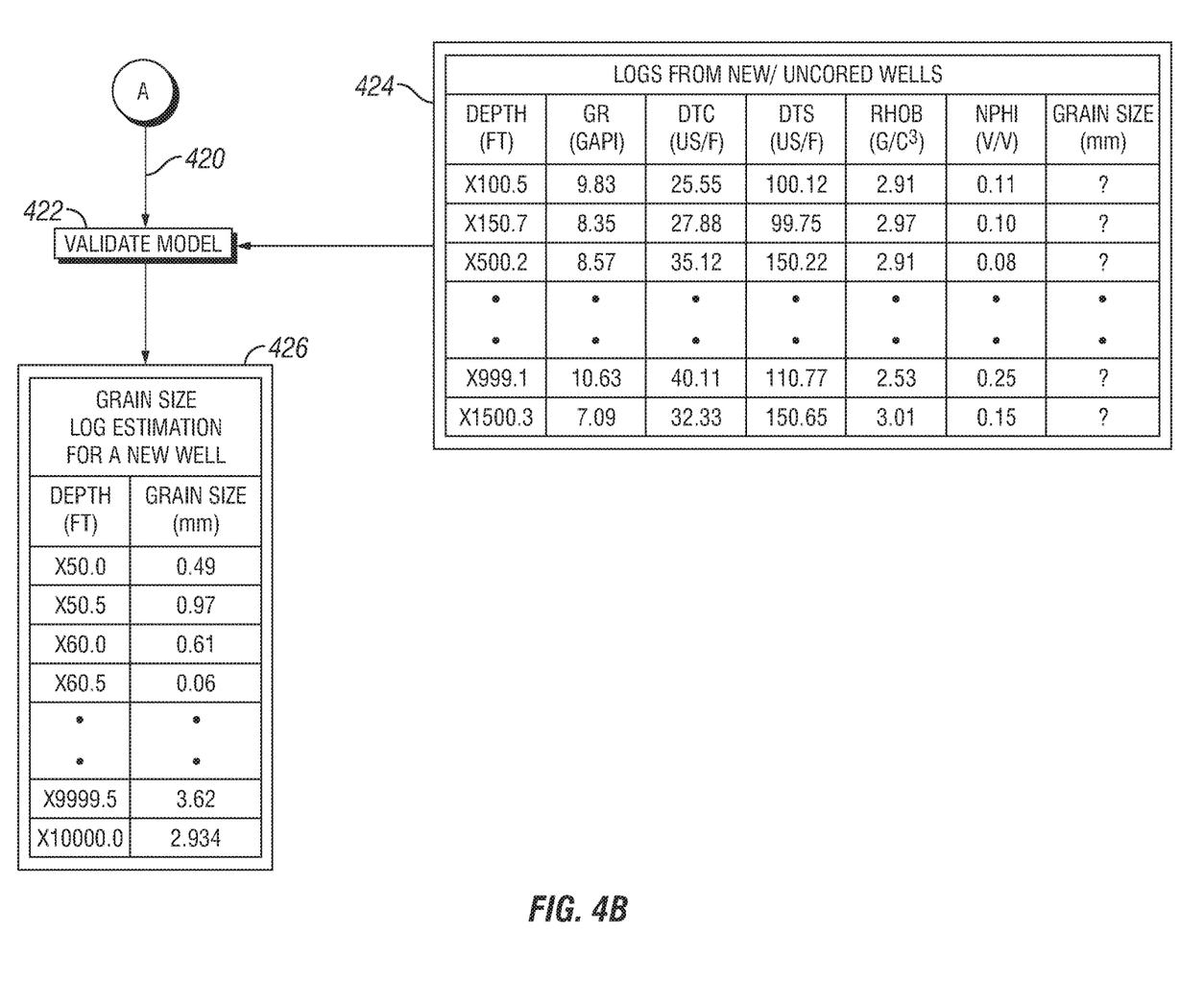

FIGS. 4A and 4B depicts a process 400 illustrating construction and operation of the machine learning model in accordance with an embodiment of the disclosure. Initially, a majority (greater than 50%) of a grain size and wireline logs data structure (block 402) may be provided to a machine learning engine (block 404). In some embodiments, 70% of a grain size and wireline log data structure may be used to train (also referred to as "calibrate") a machine learning engine. In some embodiments, the machine learning engine may be use an artificial neural network (ANN), a support vector machine (SVM), a radial basis function (RBF), fuzzy logic, or a decision tree. A machine learning model may be trained (block 406) by adjusting and optimizing learning parameters of the machine learning engine. Example learning parameters may include learning rate, number of neurons, number of layers, activation function, and weight coefficients (block 408).

The training of the machine learning engine may include creation of a mathematical relationship between the wireline logs and the estimated grain sizes. In some embodiments, each wireline log may be multiplied by a weight factor. The weight factor may be in the range of 0 to ±1 and may be obtained from the degree of correlation or significance between the wireline log and the estimated grain size. The outcome of the weighting is used to determine the effect a wireline log has on the relationship. A function $f$, such as a sigmoid or Gaussian function, may be used to transform the input space to a high-dimensional nonlinear space to match the nature of the subsurface data. A simplified example mathematical relationship is shown in Equation 1:

$$Y = f(a_1 X_1 + a_2 X_2 + \ldots + a_6 X_6) \tag{1}$$

Where Y is the output (grain size), $a_1 \ldots a_6$ are the weighting factors, $X_1 \ldots X_6$ are the wireline logs, and f is the activation function (such as a Gaussian or sigmoid function). A Gaussian function is shown in Equation 2:

$$f(x) = e^{-x^2} \tag{2}$$

Where x is each of the input wireline logs.

A sigmoid function is shown in Equation 3:

$$f(x) = \frac{1}{1 + e^{-x}} \tag{3}$$

Where x is each of the input wireline logs. As will be appreciated, some of the learning parameters, such as number of layers and number of neurons, may be used to fit the activation function to the training data.

The trained machine learning model produced by the machine learning engine may then be validated (block 410) using a minority (less than 50%) of the grain size and wireline log data structure (block 412). In some embodiments, 30% of a grain size and wireline log data structure may be used to validate a machine learning engine. The validation may include evaluating an error (for example, a residual) against a threshold (decision block 414). If the error is greater than the threshold (line 416), the learning parameters may be adjusted (block 418) and the machine learning model may continue to be trained (block 406).

In some embodiments, the input portion (wireline logs) of the validation minority of the grain size and wireline log data structure may be provided to the mathematical relationship. The output (grain size) is estimated using the activation function. The estimated output is then compared with the actual output portion (grain size) of the validation minority of the grain size and wireline log data structure to determine a residual. If the residual is greater than a threshold, the learning parameters are adjusted and the validation is repeated until the residual is less than the threshold.

As shown by connection block A, the process 400 is further described with reference to FIG. 4B. If the error is not greater than the threshold (line 420), the machine learning model is validated (block 422). After a validated machine learning model (block 422) is generated, wireline logs 424 from a well may be obtained. The validated machine learning model (block 422) may produce a continuous grain size log (block 426) for the new or uncored well. The grain size log (block 426) produced by the machine learning model may include reservoir scale grain size determinations at continuous depths at a particular resolution (for example, every 0.5 feet, every foot, or every 2 feet). In some embodiments, for example, the grain size log may include grain sizes for depths of every 0.5 ft. For example, the grain size log (block 426) shown in FIG. 4B includes a grain size of 0.49 mm for a depth of 50 ft, a grain size log 0.97 mm for a depth of 50.5 ft, and so on.

In some embodiments, the process 400 may include retraining (that is, recalibration) of the machine learning model. For example, when additional grain size estimations and wireline logs are available, they may added to the grain size and wireline logs data structure. Using the updated grain size and wireline logs data structure, new learning parameters may be derived based on the additional grain size estimations and wireline logs to produce an updated machine learning model.

Figure 5:
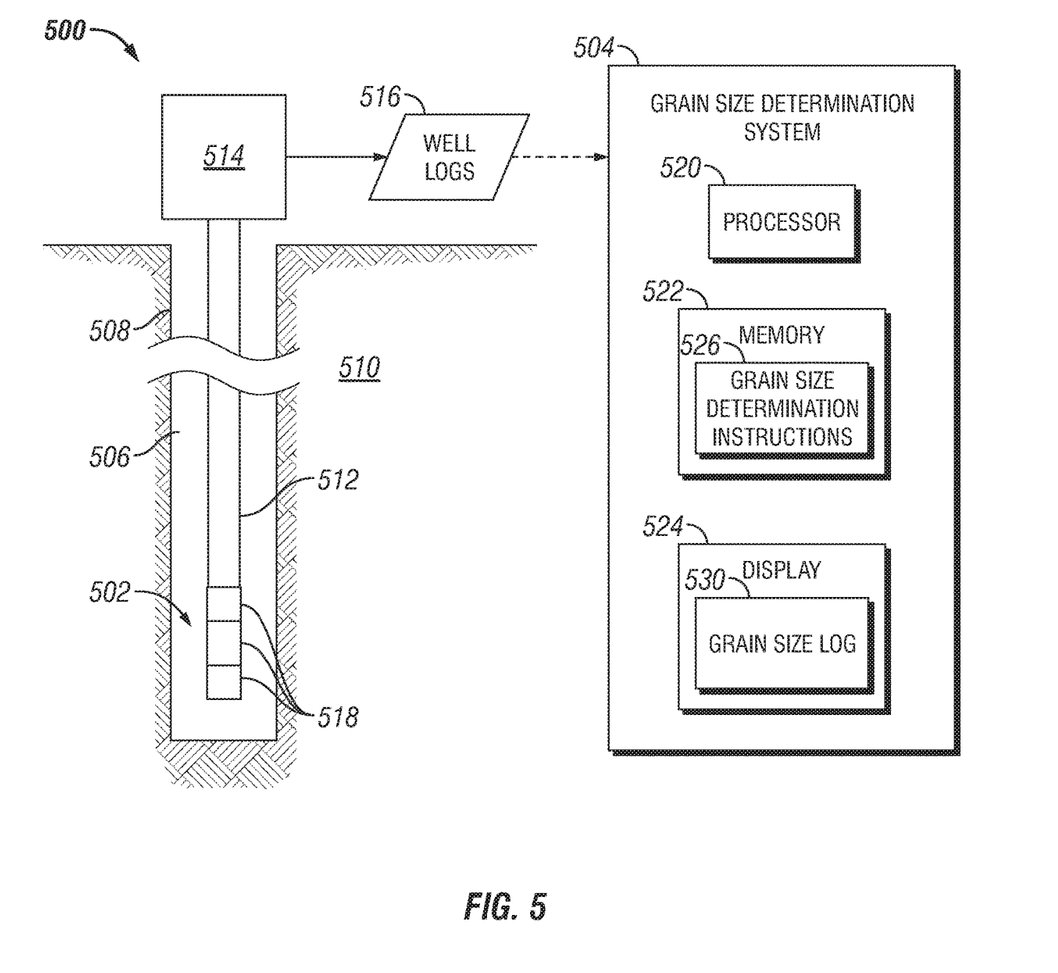
FIG. 5 is a schematic diagram of an example well site having a wireline tool and a grain size determination system in accordance with an embodiment of the disclosure.

FIG. 5 depicts an example well site 500 having a wireline tool 502 and a grain size determination system 504 in accordance with an embodiment of the disclosure. In the illustrated embodiment, the wireline tool 502 is inserted in a wellbore 506 of a well 508 extending into a formation 510. The wellbore 506 may be, for example, the wellbore 506 of an exploration well, a crestal well, or other types of wells drilled to explore a reservoir.

As shown in FIG. 5, the wireline tool 502 is suspended on a wireline 512. The wireline 512 may include a conductor and may enable data transmission between the wireline tool 502 and a wireline monitoring and control system 514. The wireline 512 may be raised and lowered within the well 508 to various depths using devices known in the art, such as a reel and drum apparatus in a service truck having the various components of a wireline system. The monitoring and control system 514 may control operation of the wireline tool 502 in the wellbore 506 and may receive data from wireline tool 502 to produce wireline logs 516. For example, the monitoring and control system 514 may include one or more computer systems or devices. As discussed in the disclosure, the wireline logs 516 may include gamma ray (GR), neutron porosity (NPHI), sonic (DT), deep resistivity (RTD), shallow resistivity (RTS), and density (RHOB) logs.

The wellbore 506 may include any form of a hole formed in a geologic formation, such as for the purpose of locating and extracting hydrocarbons or other resources from the formation 510. For example, the formation 510 may include an oil and gas reservoir, and the wellbore 506 may include a wellbore drilled into the formation 510 for the purpose of locating and obtaining information about the oil, gas and other hydrocarbons in the reservoir.

Although the embodiment shown in FIG. 5 depicts a wireline tool, in other embodiments other well logging tools may be used. For example, in some embodiments, similar tools (or tools having similar measurement capabilities) can be incorporated into a logging-while-drilling LWD apparatus. A LWD tool may have components or functionality in common with wireline tools (for example, transmitting and receiving antennas and sensors), but may be designed and constructed to endure and operate during drilling.

The wireline tool 502 may include modules 518 that enable the measurement of various properties and generation of the well logs. For example, the wireline tool 502 may include electromagnetic (resistivity) tools, nuclear tools, acoustic tools, and nuclear magnetic resonance (NMR) tools, and other tools. Such modules 518 may include known components for operation of these modules, such as sensors, antennas, receivers, transmitters, and fluid samplers. In some embodiments, the wireline tool 502 may measure and produce logs of resistivity, porosity, and other measurements that may be used by the grain size determination system 504 to determine grain sizes of rocks of the formation 510, as described in the disclosure. The grain sizes of formation rocks may then be used to further plan and perform exploration, management, and assessment of the reservoir.

FIG. 5 also depicts components of the grain size determination system 504 in accordance with an embodiment of the disclosure. As shown in FIG. 5, the grain size determination system 504 may include a processor 520, a memory 522, and a display 524. It should be appreciated that the grain size determination system 504 may include other components that are omitted for clarity, such as a network interface or an input device.

The processor 520 (as used the disclosure, the term "processor" encompasses microprocessors) may include one or more processors having the capability to receive and process wireline log data, such as data generated from the wireline tool 502. In some embodiments, the processor 520 may include an application-specific integrated circuit (AISC). In some embodiments, the processor 520 may include a reduced instruction set (RISC) processor. Additionally, the processor 520 may include single-core processors and multicore processors and may include graphics processors. Multiple processors may be employed to provide for parallel or sequential execution of one or more of the techniques described in the disclosure. The processor 520 may receive instructions and data from a memory (for example, memory 522).

The memory 522 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 522 may be accessible by the processor 520. The memory 522 may store executable computer code. The executable computer code may include computer program instructions for implementing one or more techniques described in the disclosure. For example, the executable computer code may include grain size determination instructions 526 to implement one or more embodiments of the present disclosure. In some embodiments, the grain size determination instructions 526 may implement one or more elements of the process 400 described supra and illustrated in FIGS. 4A and 4B. In some embodiments, the grain size determination instructions 526 may receive, as input, wireline log data and provide, as output, a grain size log having grain size determinations for the formation 510. The outputs may be stored in the memory 522.

The grain size determination system 504 may include or have access to a machine learning model for implementation of embodiments of the disclosure. For example, in some embodiments the memory 522 of the grain size determination system may include instructions defining a machine learning model executable by the processor 520. In other embodiments, the grain size determination system 504 may access a machine learning model over a wired or wireless network using a network interface, such that inputs may be provided to and outputs may be received from the machine learning model over the network.

The display 524 may include a cathode ray tube (CRT) display, liquid crystal display (LCD), an organic light emitting diode (OLED) display, or other suitable display. The display 524 may display a user interface (for example, a graphical user interface). In accordance with some embodiments, the display 524 may be a touch screen and may include or be provided with touch sensitive elements through which a user may interact with the user interface. In some embodiments, the display 524 may display a grain size log 530 as determined by the grain size determination instructions 526 in accordance with the techniques described in the disclosure.

In some embodiments, the grain size determination system 504 may include a network interface (not shown) that may provide for communication between the grain size determination system 504 and other devices. The network interface may include a wired network interface. The network interface may communicate with networks, such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (for example, IEEE 802.11 standards), and other standards, protocols, and technologies.

In some embodiments, the grain size determination system 504 may be coupled to an input device (for example, one or more input devices). The input devices may include, for example, a keyboard, a mouse, a microphone, or other input devices. In some embodiments, the input device may enable interaction with a user interface displayed on the display 524. For example, in some embodiments, the input devices may enable the entry of inputs to a process for determining a continuous grain size log and parameters used in the process (for example, learning parameters of a selected machine learning engine).

Advantageously, the grain size log produced by the grain size determination system includes continuous grain sizes at the reservoir scale (as opposed to the pore scale), such as at a depth of every 0.5 feet. The continuous grain size log may thus be considered representative of a reservoir and may be used to predict other reservoir properties, such as depositional environment, porosity, permeability, and lithofacies. For example, the continuous grain size log may be used as inputs to an automated core description, facie prediction, depositional modeling, basin modeling, or Kozeny-Carman equation for permeability estimation.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method for determining grain size of reservoir rock in a hydrocarbon reservoir, comprising:
   extracting a plurality of core samples from a first well, each core sample extracted from a different depth in the well;
   cutting a respective plurality of sections from the plurality of core samples;
   determining a grain size from each section of the plurality of sections to determine a plurality of discrete grain sizes at a respective plurality of depths in the first well;
   obtaining a first wireline log from the first well;
   combining the first wireline log and the plurality of discrete grain sizes at the plurality of depths in the first well to produce a structured data set;
   generating a machine learning model using the structured data set;
   inserting a wireline tool into a second well;
   generating a second wireline log from measurements obtained using the wireline tool; and
   determining, using the second wireline log and the machine learning model, a continuous grain size log comprising a plurality of grain sizes and a respective plurality of continuous depths in the second well, wherein determining the grain size from each section of the plurality of sections to determine the plurality of grain sizes at the plurality of depths in the first well comprises:
   determining a first image of the section, the first image acquired with plane-polarized light;
   determining a feature vector for each respective pixel of the first image, the feature vector including color components corresponding to each respective pixel;
   determining a plurality of regions of the section by clustering the pixels of the first image based on the feature vector for each respective pixel;
   determining a second image of the section, the second image acquired with cross-polarized light;
   combining the first image and the second image images of the section to produce a composite image,
   generating a mask image based on the plurality of regions;
   segmenting grains based on the plurality of regions, wherein segmenting grains comprising combining the composite image and the mask image;
   determining a grain size of one of the segmented grains.

2. The method of claim 1, wherein obtaining a first wireline log from the first well comprises:
   inserting a wireline tool into the first well; and
   generating the first wireline log from measurements obtained using the wireline tool.

3. The method of claim 1, wherein the first wireline log comprises at least one of a gamma ray (GR) log, a neutron porosity (NPHI) log, a sonic (DT) log, a deep resistivity (RTD) log, a shallow resistivity (RTS) log, and a density (RHOB) log.

4. The method of claim 1, wherein the second wireline log comprises at least one of a gamma ray (GR) log, a neutron porosity (NPHI) log, a sonic (DT) log, a deep resistivity (RTD) log, a shallow resistivity (RTS) log, and a density (RHOB) log.

5. The method of claim 1, wherein the machine learning model comprises an artificial neural network (ANN), a support vector machine (SVM), a radial basis function (RBF), fuzzy logic, or a decision tree.

6. The method of claim 1, wherein each section of the plurality of sections has a thickness of 30 microns.

7. A system for determining a grain size of reservoir rock in a hydrocarbon reservoir, comprising:
   a plurality of sections cut from a respective plurality of core samples from a first well, each core sample extracted from a different depth in the first well, the plurality of sections used to determine a grain size from each section of the plurality of sections to produce a plurality of discrete grain sizes at a respective plurality of depths in the first well;
   a first wireline log from the first well;
   a non-transitory computer-readable medium, the medium having executable code stored thereon, the executable code comprising a set of instructions that causes a processor to perform operations comprising:

combining the first wireline log and the plurality of discrete grain size at the respective plurality of depths in the first well to produce a structured data set;
generating a machine learning model using the structured data set;
receiving a second wireline log from a second well; and
determining, using the second wireline log and the machine learning model, a continuous grain size log comprising a plurality of grain sizes and a respective plurality of continuous depths in the second well, wherein the grain size from each section of the plurality of sections is determined by:
determining a first image of the section, the first image acquired with plane-polarized light;
determining a feature vector for each respective pixel of the first image, the feature vector including color components corresponding to each respective pixel;
determining a plurality of regions of the section by clustering the pixels of the first image based on the feature vector for each respective pixel;
determining a second image of the section, the second image acquired with cross-polarized light;
combining the first image and the second image images of the section to produce a composite image,
generating a mask image based on the plurality of regions;
segmenting grains based on the plurality of regions, wherein segmenting grains comprising combining the composite image and the mask image;
determining a grain size of one of the segmented grains.

8. The system of claim 7, wherein the first wireline log comprises at least one of a gamma ray (GR) log, a neutron porosity (NPHI) log, a sonic (DT) log, a deep resistivity (RTD) log, a shallow resistivity (RTS) log, and a density (RHOB) log.

9. The system of claim 7, wherein the second wireline log comprises at least one of a gamma ray (GR) log, a neutron porosity (NPHI) log, a sonic (DT) log, a deep resistivity (RTD) log, a shallow resistivity (RTS) log, and a density (RHOB) log.

10. The system of claim 7, wherein the machine learning model comprises an artificial neural network (ANN), a support vector machine (SVM), a radial basis function (RBF), fuzzy logic, or a decision tree.

11. The system of claim 7, comprising a wireline tool operable to generate the second wireline log.

12. The system of claim 7, wherein the structured data set comprises a database.

13. The system of claim 7, wherein each section of the plurality of sections has a thickness of 30 microns.

14. A non-transitory computer-readable medium, the medium having executable code stored thereon, the executable code comprising a set of instructions that causes a processor to perform operations comprising:
receiving a plurality of estimated grain sizes, each grain size estimated from a section of the plurality of sections cut from a respective plurality of core samples from a first well, each core sample extracted from a different depth in the first well;
receiving a first wireline log from the first well;
combining the first wireline log and the plurality of discrete grain sizes at a respective plurality of depths in the first well to produce a structured data set;
generating a machine learning model using the structured data set;
receiving a second wireline log from a second well; and
determining, using the second wireline log and the machine learning model, a continuous grain size log comprising a plurality of grain sizes and a respective plurality of continuous depths in the second well, wherein determining the grain size from each section of the plurality of sections to determine the plurality of grain sizes at the plurality of depths in the first well comprises:
determining a first image of the section, the first image acquired with plane-polarized light;
determining a feature vector for each respective pixel of the first image, the feature vector including color components corresponding to each respective pixel;
determining a plurality of regions of the section by clustering the pixels of the first image based on the feature vector for each respective pixel;
determining a second image of the section, the second image acquired with cross-polarized light;
combining the first image and the second image images of the section to produce a composite image,
generating a mask image based on the plurality of regions;
segmenting grains based on the plurality of regions, wherein segmenting grains comprising combining the composite image and the mask image;
determining a grain size of one of the segmented grains.

15. The computer-readable medium of claim 14, wherein the first wireline log comprises at least one of a gamma ray (GR) log, a neutron porosity (NPHI) log, a sonic (DT) log, a deep resistivity (RTD) log, a shallow resistivity (RTS) log, and a density (RHOB) log.

16. The computer-readable medium of claim 14, wherein the second wireline log comprises at least one of a gamma ray (GR) log, a neutron porosity (NPHI) log, a sonic (DT) log, a deep resistivity (RTD) log, a shallow resistivity (RTS) log, and a density (RHOB) log.

17. The computer-readable medium of claim 14, wherein the machine learning model comprises an artificial neural network (ANN), a support vector machine (SVM), a radial basis function (RBF), fuzzy logic, or a decision tree.

18. The computer-readable medium of claim 14, wherein the structured data set comprises a database.

* * * * *